United States Patent [19]

Wilson et al.

[11] Patent Number: 5,792,893
[45] Date of Patent: Aug. 11, 1998

[54] METHOD FOR THE MANUFACTURE OF 1,1,1,3,3,3-HEXACHLOROPROPANE

[75] Inventors: Richard Leroy Wilson, Mulvane; Charles Richard Cupit; Rodney Lee Klausmeyer, both of Wichita, all of Kans.

[73] Assignee: Vulcan Materials Company, Wichita, Kans.

[21] Appl. No.: 677,120

[22] Filed: Jul. 9, 1996

[51] Int. Cl.[6] .................................................. C07C 17/26
[52] U.S. Cl. ........................................................ 570/257
[58] Field of Search ............................................. 570/257

[56] References Cited

U.S. PATENT DOCUMENTS 5,395,997  3/1995  Van Der Puy et al. .
5,633,413  5/1997  Van Der Puy ........................... 570/257

OTHER PUBLICATIONS

M. Belbachir et al, "Telomerization of Vinylidene Chloride", Makromol. Chem., vol. 185, No. 8 (1984), pp. 1583–1595 and English abstract.

M. Kotora et al, "Selective Additions of Polyhalogenated Compounds to Chloro Substituted Ethenes Catalyzed by a Copper Complex", React. Kinet. Catal. Lett., vol. 44, No. 2 (1991), pp. 415–419.

Asahara et al, Telomerization: II. N.M.R. Analysis of Telomers Prepared From Vinyl Compounds and Carbon Tetrachloride. Kogyo Kagaku Zasshi, 72(7) (Japan) (1969), pp. 1516–1520 and English abstract.

*Primary Examiner*—Alan Siegel
*Attorney, Agent, or Firm*—Burns, Doane, Swecker & Mathis, L.L.P.

[57] ABSTRACT

A novel method for manufacturing 1,1,1,3,3,3-hexachloropropane. Tetrachloromethane is reacted with 1,1-dichloroethene in the presence of a catalyst comprising copper and a solvent selected from a C3 to a C5 alkanenitrile. The 1,1,1,3,3,3-hexachloropropane can be separated from the reaction by-products, unconsumed reactants and catalyst and solvent, which components can be recovered and recycled back to the reactor.

33 Claims, 2 Drawing Sheets

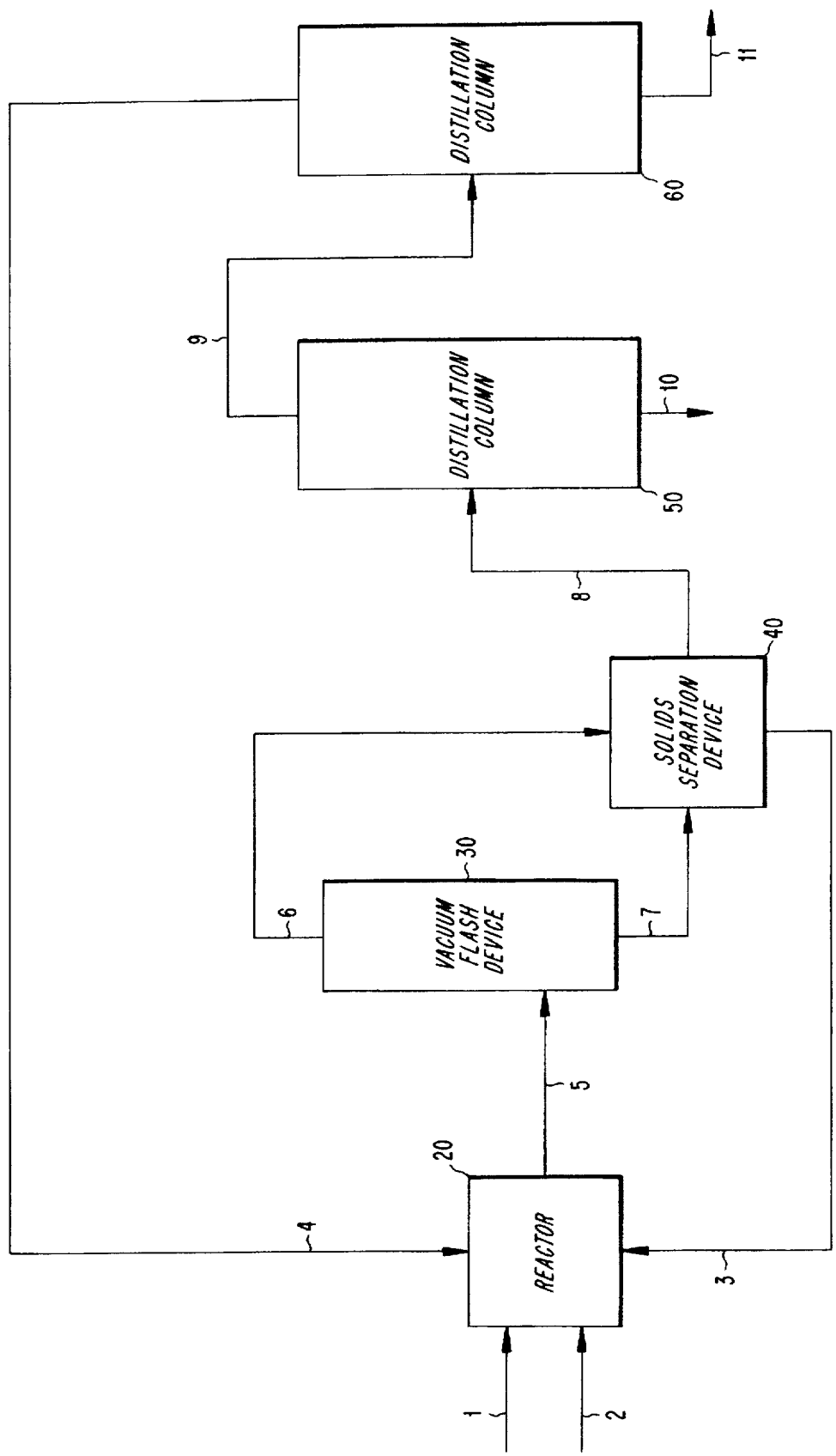

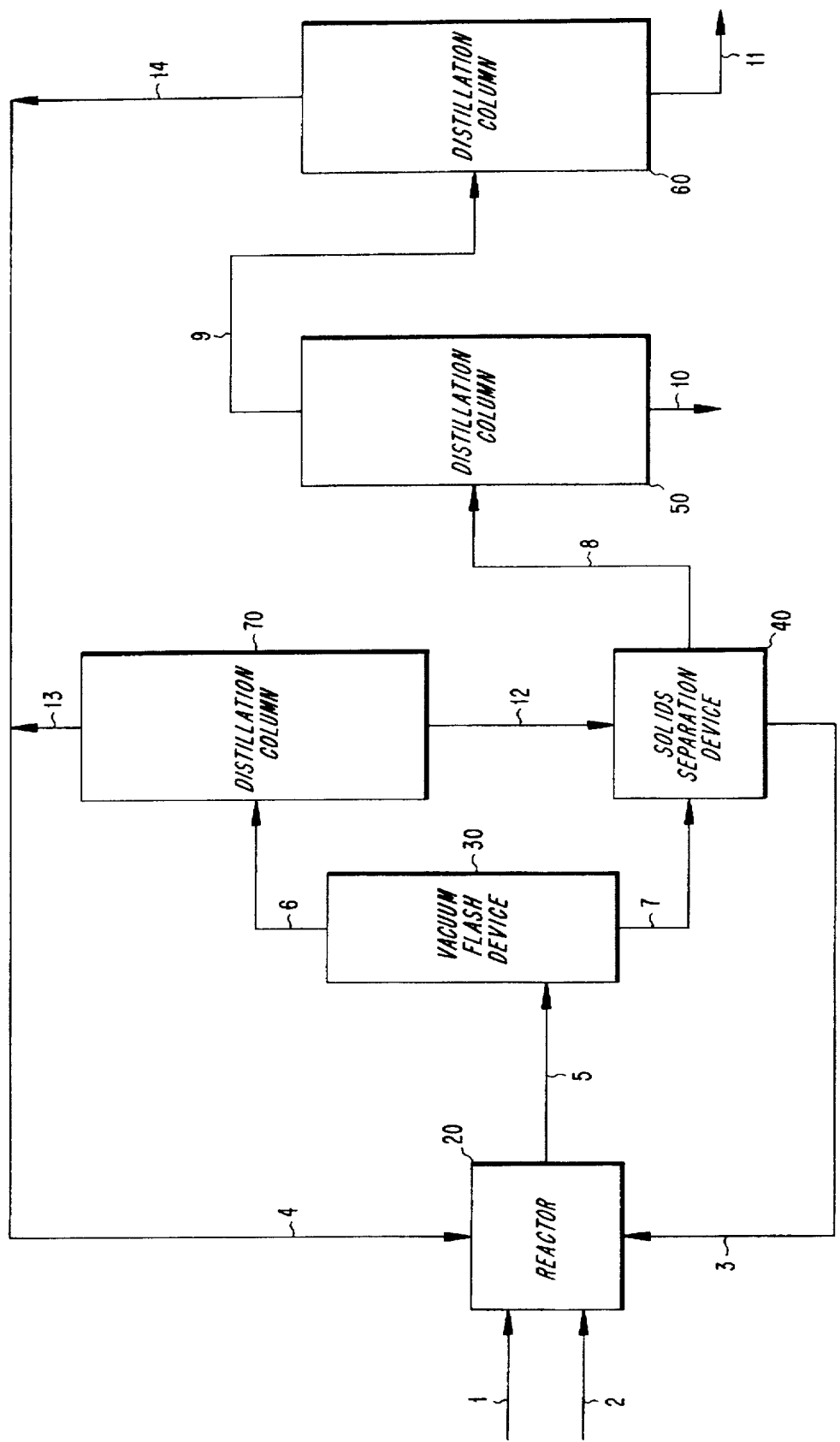

METHOD FOR THE MANUFACTURE OF 1,1,1,3,3,3-HEXACHLOROPROPANE

BACKGROUND OF THE INVENTION

1. Field of the Invention

The present invention relates to a method for manufacturing 1,1,1,3,3,3-hexachloropropane and to a method of recovery and purification thereof. The inventive method further allows for the recovery and recycle of catalyst, solvent and unconsumed reactants.

2. Description of the Related Art 1,1,1,3,3,3-hexachloropropane (HCPr) is of current interest as a potential feedstock in the manufacture of hydrofluorocarbon compounds to replace ozone depleting chlorofluorocarbons (CFC's) and hydrochlorofluorocarbons (HCFC's). CFC's and HCFC's are used in a variety of applications, e.g., refrigerants, propellants, blowing agents and solvents.

It will be appreciated that the formation of 1,1,1,3,3,3-hexachloropropane is described in the literature, both patent and otherwise. For example, among the known methods for manufacturing 1,1,1,3,3,3-hexachloropropane, M. Belbachir et al, in *Telomerization of Vinylidene Chloride*, Makromol. Chem., Vol. 185, No. 8 (1984), pp. 1583–1595, discloses reacting 1,1-dichloroethene ($CH_2=CCl_2$) with tetrachloromethane ($CCl_4$) in the presence of a copper chloride catalyst and acetonitrile solvent according to the following reaction:

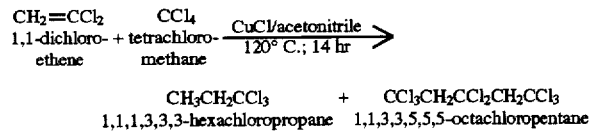

The reaction products are 1,1,1,3,3,3-hexachloropropane and other higher weight by-products, such as 1,1,1,3,3,5,5,5-octachloropentane (OCPe). The overall yield of the products is disclosed as being about 91%, based on the olefin fed.

The selectivity of HCPr versus the higher molecular weight by-products, e.g., OCPe, was found to be dependent upon the feed ratio of the 1,1-dichloroethene to tetrachloromethane. Selectivity was further found to be strongly influenced by the specific solvent used. In this regard, Belbachir et al disclose that selectivity decreases for the following solvents in the order stated: dimethylsulfoxide>acetonitrile>tetrahydrofuran>>triethylamine.

Furthermore, according to M. Kotora et al, in *Selective Additions of Polyhalogenated Compounds to Chloro Substituted Ethenes Catalyzed by a Copper Complex*, React. Kinet. Catal. Lett., Vol. 44, No. 2 (1991), pp. 415–419, tetrachloromethane was reacted with 1,1-dichloroethene in the presence of a cuprous complex catalyst with isopropylamine, to produce 1,1,1,3,3,3-hexachloropropane. The yield is disclosed as being almost exclusively 30%.

Asahara et al, *Telomerization: II. N.M.R. Analysis of Telomers Prepared From Vinyl Compounds and Carbon Tetrachloride*, Kogyo Kagaku Zasshi, 72(7) (Japan) (1969), pp. 1516–20, discloses formation of 1,1,1,3,3,3-hexachloropropane by reacting tetrachloromethane with 1,1-dichloroethene in the presence of a ferrous chloride catalyst and a butaneamine solvent.

In U.S. Pat. No. 5,395,997, to Van Der Puy et al, for forming HCPr, acetonitrile is a preferred solvent with a catalyst comprising cuprous chloride (CuCl), cupric chloride ($CuCl_2$), a mixture of cuprous chloride and cupric chloride, or cuprous iodide.

The above described processes for forming HCPr suffer from various disadvantages. For example, when an acetonitrile solvent is used with a copper chloride catalyst, large, hard, solid chunks are formed. Generally, these solid chunks are of a size ranging from fines to about ¼, inch in diameter. Such solid chunks can give rise to serious handling problems. For example, transfer of such a solvent-catalyst mixture into a reactor can be especially problematic, since clogging of process piping and pump damage result from the chunks.

When using amines as solvents in the formation of HCPr, it is known that a reaction disadvantageously occurs with chlorocarbons, especially in the presence of transition metal compounds such as copper chloride (see, J. R. Lindsay Smith et al, *Reaction of Primary Amines with Carbon Tetrachloride in the Presence of Copper (II) Acetate*, J. Chem. Soc. (B) (1970), pp. 617–623, and presumably, iron chlorides.

When used as a solvent, dimethylformamide is known to be incompatible with chlorinated hydrocarbons as a result of violent reactions. (See, *Sax's Dangerous Properties of Industrial Materials*, Ed. R. J. Lewis, Jr., 8th Ed. (1992), p. 1378). Dimethylsulfoxide was found to disappear, apparently due to decomposition, during preparation of HCPr using a copper catalyst. In addition, alcohols, such as isopropanol, react in the presence of chlorocarbons and transition metals, thereby forming hydrochloric acid, ethers, olefins and water.

SUMMARY OF THE INVENTION

Accordingly, a major object of the present invention is the provision of a simple and economical method for forming 1,1,1,3,3,3-hexachloropropane, which overcomes the above described disadvantages associated with the prior art.

Briefly, the present invention features a novel method for producing 1,1,1,3,3,3-hexachloropropane, comprising reacting tetrachloromethane and 1,1-dichloroethene in the presence of a catalyst comprising copper chloride, and a solvent selected from a C3 to a C5 alkanenitrile, wherein the tetrachloromethane, 1,1-dichloroethene, catalyst and solvent are present in relative amounts sufficient to produce 1,1,1,3,3,3-hexachloropropane.

It has been surprisingly and unexpectedly determined by the present inventors that superior results can be obtained when a C3 to a C5 alkanenitrile is employed as a solvent in the reaction of tetrachloromethane with 1,1-dichloroethene in the presence of a copper chloride catalyst. Mixtures of such a solvent with copper chloride catalysts were found to form homogeneous solutions or fine slurries, which are especially easy to transfer into a reactor. This is especially surprising in view of the fact that prior art processes employing acetonitrile, for example, result in the formation of large, hard solid chunks. Since the use of acetonitrile, as well as the other conventionally used solvents, result in disadvantages in a process for preparing 1,1,1,3,3,3-hexachloropropane, there would have been no motivation for one skilled in the art to employ a C3 to C5 alkanenitrile solvent in a process as claimed. Nor would there have been any expectation of the superior results obtained by using such solvents.

The inventive method further provides for the separation/purification of the 1,1,1,3,3,3-hexachloropropane from the reaction by-products, unconsumed reactants, catalyst and solvent.

Moreover, in accordance with the inventive method, one or more of the catalyst, the solvent, the unreacted tetrachloromethane, and the unreacted 1,1-dichloroethene can be recovered and recycled back to the reactor.

BRIEF DESCRIPTION OF THE DRAWINGS

The invention will be described in greater detail with reference to the accompanying drawing, wherein:

FIG. 1 is a schematic representation of a process flow according to one aspect of the present invention.

FIG. 2 is a schematic representation of a process flow according to a second aspect of the present invention.

DETAILED DESCRIPTION OF THE PREFERRED EMBODIMENTS OF THE INVENTION

1. Manufacture of 1,1,1,3,3,3-hexachloropropane:

More particularly, according to the present invention, 1,1,1,3,3,3-hexachloropropane is produced by the liquid phase reaction of tetrachloromethane with 1,1-dichloroethene. The reaction takes place in the presence of a copper chloride catalyst and solvent.

Preferably, the catalyst is either cuprous chloride (CuCl), cupric chloride ($CuCl_2$), or a mixture of cuprous and cupric chlorides.

The solvent used in the inventive method is a C3 to C5 alkanenitrile, such as propanenitrile (ethyl cyanide, $C_2H_5CN$), butanenitrile (propyl cyanide, $CH_3(CH_2)_2CN$) and pentanenitrile (butyl cyanide, $CH_3(CH_2)_3CN$). Relatively inexpensive, stable C3 to C5 alkanenitrile solvents having boiling points less than 208° C., i.e., the boiling point of 1,1,1,3,3,3-hexachloropropane, are preferred. These alkanenitriles may be substituted or unsubstituted. Examples of suitable substituents include alkyl and alkoxy groups. As used herein, "alkyl" refers to cyclic, branched, or straight chain alkyl groups containing only carbon and hydrogen. "Alkoxy" refers to straight or branched chain alkoxy groups, such as methoxy and ethoxy. For example, 2-methylpropanenitrile and 3-methoxypropanenitrile are suitable solvents. Fluorine can also be used as an alkanenitrile substituent. Butanenitrile is the preferred solvent of the present invention.

While the amount of solvent used is not critical, the solvent is employed in an amount sufficient to promote the reaction at a commercially useful rate. The tetrachloromethane, 1,1-dichloroethene, copper chloride catalyst and solvent are all present in relative amounts sufficient to produce 1,1,1,3,3,3-hexachloropropane.

The reaction is preferably carried out at a temperature in the range of from about 80° to 150° C. More preferably, the temperature is in the range of from about 110° to 150° C.

The molar feed ratio of tetrachloromethane to 1,1-dichloroethene should be sufficiently high to provide an acceptable selectivity for 1,1,1,3,3,3-hexachloropropane versus the 1,1,1,3,3,5,5,5-octachloropentane byproduct. By acceptable selectivity of HCPr versus OCPe is intended a weight ratio of HCPr:OCPe in the reaction product of greater than 10:1. A preferred selectivity is 14:1 and a more preferred selectivity is 19:1.

While selectivity increases with increasing molar feed ratio of tetrachloromethane to 1,1-dichloroethene, it is also inversely related to conversion. For example, at a given feed ratio of tetrachloromethane:1,1-dichloroethene, a higher selectivity is obtained at low conversion than at high conversion. However, lower conversion requires more extensive recycling of carbon tetrachloride.

With the above in mind, molar ratios in the range of down to about 0.5:1 to about 3.3:1 tetrachloromethane:1,1-dichloroethene work well, but at low conversion levels. Thus, taking both conversion and selectivity into consideration, molar ratios in the range of from about 1.0:1 to about 3.3:1 tetrachloromethane:1,1-dichloroethene are preferred, with molar ratios in the range of from about 1.1:1 to 2.0:1 tetrachloromethane: 1,1-dichloroethene being more preferred.

Also, the copper chloride catalyst to 1,1-dichloroethene molar feed ratio is preferably selected so as to provide a suitable reaction rate to enable production of the desired product in an economical manner. In general, the molar feed ratio is in the range of from about 0.01:1 to 0.50:1 copper chloride:1,1-dichloroethene, preferably about 0.06:1 to 0.24:1. However, in practice, optimal ratios are to be determined by economic considerations, such as reactor size and the cost of copper chloride catalyst recycling.

A suitable reaction rate for the process of the invention is generally in the range of from about 0.05 to 2.0 gmole/hr-liter, and preferably in the range of about 0.2 to 1.2 gmole/hr-liter.

Moreover, the molar feed ratio of the solvent:1,1-dichloroethene is preferably sufficient to allow an adequate amount of copper chloride catalyst to be dissolved in the liquid. In general, molar ratios in the range of from about 0.05:1 to 10:1, preferably about 0.5:1 to 3.0:1, are encompassed by the invention, while molar ratios in the range from about 1.4:1 to 2.0:1 were found to be particularly preferable. Higher molar feed ratios may be used. However, the process of the invention will then require additional subsequent separation steps, making the process less economical.

It has also been determined that the inventive method is particularly flexible in the manner in which the reaction can performed. For example, the reaction can be performed in a batch mode. In such a case, the reactants, catalyst and solvent can be first charged into the reactor, and then the reaction performed. Upon completion of the reaction, the contents of the reactor are removed.

Additionally, the reaction can be run in a semibatch mode, wherein one or more of the reactants, catalyst or solvent are added to the reactor either continuously or periodically. For example, the tetrachloromethane, copper chloride and solvent can be initially charged into the reactor, while the 1,1-dichloroethene is added to the reactor either continuously or intermittently.

The reaction can further be run in a continuous mode. In such a case, the reactants, catalyst and solvent are continuously introduced into a reactor, while the reaction products are continuously removed therefrom.

2. Separation/Purification of 1,1,1,3,3,3-hexachloropropane:

A further aspect of the present invention involves a method for the recovery and purification of the 1,1,1,3,3,3-hexachloropropane formed through the above described liquid phase reaction. This aspect of the process allows for the recovery and recycle of the catalyst, solvent and unreacted 1,1-dichloroethene and tetrachloromethane. As a result, 1,1,1,3,3,3-hexachloropropane of high purity can be obtained, and the process can be efficiently and economically run.

This aspect of the invention will now be described with reference to FIG. 1, which illustrates the primary process steps of the inventive method. The system on which the inventive method is practiced comprises reactor 20, vacuum flash device or column 30, settling vessel, filter, hydrocyclone, centrifuge or other suitable solids separation device 40, and distillation columns 50 and 60.

The reactants described above, 1,1-dichloroethene and tetrachloromethane, are fed to reactor 20 through lines 1 and 2, respectively. In reactor 20, the reactants are contacted in the liquid phase in the presence of the copper chloride catalyst and C3 to C5 alkanenitrile solvent, to form HCPr and a small amount of OCPe.

Reactor effluent 5 is fed to a vacuum flash vessel or column 30. The reactor effluent is then separated into at least two portions. The first portion comprises components having a boiling point lower than that of HCPr, and the second portion comprises components having a boiling point greater than or equal to that of HCPr. The components in effluent 5 having a boiling point lower than HCPr, i.e., the first portion, are flashed overhead as stream 6, which can optionally be recycled to reactor 20. The components in effluent 5 having a boiling point lower than HCPr are 1,1-dichloroethene, carbon tetrachloride and the C3 to C5 solvent.

The bottoms 7 from vacuum flash vessel or column 30, i.e., the second portion, consists of a liquid phase containing both HCPr and OCPe, as well as a solids phase of fine copper chloride particles. The bottoms 7 can be cooled, and the solids removed therefrom by, e.g., sedimentation and/or filtration, using a settling vessel, filter, hydrocyclone, centrifuge or other suitable solids separation device 40.

Preferably, the solids separation device is a settling vessel and a filter. After filling the settling vessel with bottoms 7, the solids are allowed to settle out. Then, the liquid is drawn off and filtered. Solvent can then be added to dissolve the copper chloride.

The settling vessel can be provided with an agitation device to mix the solids and solvent. The recovered copper chloride can be re-dissolved by the solvent, i.e., the C3 to C5 alkanenitrile, contained in the light ends 6 from the vacuum flash vessel or column 30. This solvent and redissolved catalyst in line 3 can then be optionally recycled to reactor 20.

Subsequent to removal of the solids, liquid stream 8 can be fed to distillation column 50, where the lower boiling point compound(s), including HCPr, are distilled overhead as line 9. The higher boiling compounds, primarily OCPe, is removed in bottoms 10.

The overhead product 9 from distillation column 50 can next be fed to distillation column 60, where remaining quantities of lower boiling compounds 4 can be distilled overhead as line 4. These compounds can then be recycled to reactor 20. Purified HCPr remains as bottoms product 11.

Persons of ordinary skill in the art can readily understand that various modifications of the separations equipment can be made within the scope of the invention. For example, it is envisioned that the sequence of columns 50 and 60 can be reversed, such that the lower boiling compounds are removed prior to removing the higher boiling compounds. Similar additional modifications, for example, can also be made for the present invention.

A further embodiment of the invention is described below with reference to FIG. 2. According to this embodiment, distillation column 70 can be added to the process described above, with reference to FIG. 1, to separate vinylidene chloride and carbon tetrachloride from the solvent. Overhead product 6 from the vacuum flash vessel or column 30 is fed to distillation column 70. Column 70 separates the 1,1-dichloroethene and carbon tetrachloride overhead as light ends 13 from the solvent as bottoms 12. Light ends 13 from column 70 and light ends 14 from column 60 can be optionally recycled to the reactor. Moreover, the solvent in bottoms 12 can be used to redissolve the copper chloride as stream 3, which can then be recycled to reactor 20.

In order to further illustrate the present invention and the advantages thereof, the following specific examples are given, it being understood that same are intended only as illustrative and in no way limitative.

EXAMPLE 1:

32 g of cuprous chloride was mixed with 547 g of butanenitrile. The mixture was then poured into a one-gallon Pfaudler glass-lined reactor through a ½ inch pipe opening. Next, 1637 g of tetrachloromethane and 516 g of 1,1-dichloroethene were added to the reactor. The headspace of the reactor was purged of air by repeated pressurization and depressurization steps with nitrogen. The mixture was then heated at about 99° C. for 1.7 hours, cooled, and then withdrawn from the reactor through the bottom nozzle thereof (also ½ inch pipe size).

The reactor effluent was a black liquid containing traces of solids. Analysis by gas chromatography showed the liquid to contain 4.1 wt. % 1,1,1,3,3,3-hexachloropropane and 0.02 wt. % 1,1,1,3,3,5,5,5-octachloropentane, by weight. The yields of HCPr and OCPe, estimated using a forced-weight mass balance calculation, were 8.2% and 0.06%, respectively, based on the weight of 1,1-dichloroethene fed. Moreover, The space-time yield of HCPr was 0.12 g-moles per liter per hour, and the weight ratio of HCPr to OCPe in the product was 203. The results are summarized in Table 1.

EXAMPLES 2–13:

The procedure used in Example 1 was repeated, except for the difference that temperature and feed ratios of the reactants were varied to observe the effect thereof on HCPr and OCPe yields, as well as on the selectivity of the reaction.

As can be seen from Table 1, HCPr and OCPe yields generally increase with an increase in temperature. In contrast, feed ratios were found to have a relatively minor effect on yield.

Moreover, a general trend for selectivity, as measured by the weight ratio of HCPr to OCPe obtained, was found to decline with an increase in conversion.

EXAMPLE 14:

34 g of cuprous chloride was mixed with 477 g of propanenitrile, and this mixture was then added to the Pfaudler reactor. 1745 g of tetrachloromethane and 548 grams of 1,1-dichloroethene were next added to the reactor. The headspace was purged of air, and the mixture was first heated at 100° C. for 2.2 hours, and next at 118° C. for 2.6 hours. After allowing the reaction mixture to cool, the reactor effluent was removed and found to be a black liquid containing traces of solids. The solids were less than 1 mm in size, and the concentration was approximately less than 0.1% based on the total weight of reactor effluent. The yields and selectivity were as shown in Table 1.

EXAMPLE 15 (Comparative):

The procedure used in Example 1 was repeated, except for the difference that the catalyst and solvent used were 73 g of cuprous chloride mixed with 372 g of acetonitrile.

Unlike the examples using a propanenitrile or butanenitrile solvent, the mixture of acetonitrile and cuprous chloride contained large hard chunks of solids. The solids were sufficiently large to plug a ½ inch pipe having an inner diameter of about 0.6 inch. The particles ranged in size from fines to about ¼ inch in diameter. The solids constituted about 2.5% of the total materials charged to the reactor.

These solids collected and clogged the inlet nozzle of the reactor. The mixture was added to the reactor after disassembling the inlet piping and reconfiguring it in a shorter and straighter manner. The chunks were tamped through the piping with a rod. The reaction was completed as described above in Example 1.

The product was in the form of a slurry, and significantly less material was recovered than was initially added to the reactor. During subsequent rinsing of the reactor (a standard procedure in all of the examples), the bottom outlet of the reactor was clogged with solids. The results are summarized in Table 1.

As can be seen in this table, selectivity of 1,1,1,3,3,3-hexachloropropane was significantly lower for this comparative example than in Example 3 according to the inventive method in which the solvent, butanenitrile, was used.

Moreover, the serious handling problems experienced with acetonitrile were surprisingly not experienced when using either propanenitrile or butanenitrile as solvents. In contrast to the acetonitrile/catalyst mixture of the comparative example, the mixtures of propanenitrile or butanenitrile solvents with copper chloride catalysts were found to form homogeneous solutions or fine slurries. Consequently, the solvent/catalyst mixture was easily transferred into the reactor, with no blockage or clogging of the reactor piping.

According to these experiments, liquid was refluxed under vacuum in glass equipment for set periods and at various temperatures. Samples were taken and the compositions thereof analyzed at the beginning and end of each period.

For purified HCPr, corresponding to stream 11 in FIG. 1, the decomposition rate of HCPr was found to be less than 0.1%/hour at 148.9° C. (300° F.) based on the weight of HCPr fed. However, for temperatures of 176.7° C. (350° F.) and 204.4° C. (400° F.), the decomposition rate rose to levels of about 2.4%/hour and about 5.0%/hour, respectively. Furthermore, increased levels of 1,1,1,3,3-pentachloropropene, the expected dehydrochlorination product of HCPr, were observed in those experiments taking place at temperatures of 176.7° C. (350° C.) and 204.4° C. (400° C.).

EXAMPLE 17:

Similar experiments to those described above with respect to Example 16 were performed in order to determine the rate of thermal decomposition of HCPr and OCPe in an unpurified stream. In these experiments, the material sampled was that corresponding to stream 8, i.e., the material remaining after filtering the bottoms 7 from the flashing unit 30.

OCPe decomposition was found to be 11%/hour at 121.1° C. (250° F.), rising to 43%/hour at 148.9° C. (300° F.), and

TABLE 1

| Example | | 1 | 2 | 3 | 4 | 5 | 6 | 7 | 8 |
|---|---|---|---|---|---|---|---|---|---|
| Elapsed Time (Hr) | | 1.7 | 1.75 | 1.60 | 1.60 | 1.60 | 1.60 | 1.60 | 1.60 |
| Avg. Temperature (°C.) | | 99 | 97 | 122 | 132 | 131 | 99 | 99 | 100 |
| Max. Temperature (°C.) | | 105 | 100 | 129 | 137 | 139 | 102 | 102 | 107 |
| Feeds | 1,1-dichloroethene (grams) | 516 | 931.0 | 529.6 | 414.0 | 581.0 | 578.0 | 466.0 | 576.8 |
| | butanenitrile (grams) | 547 | 186.2 | 556.0 | 487.4 | 690.8 | 419.5 | 668.7 | 794.1 |
| | copper (I) chloride (grams) | 32 | 32.3 | 64.2 | 42.2 | 119.8 | 74.4 | 30.3 | 72.1 |
| | acetonitrile (grams) | — | — | — | — | — | — | — | — |
| | propanenitrile (grams) | — | — | — | — | — | — | — | — |
| | tetrachloromethane (grams) | 1637 | 1639.6 | 1682.3 | 2139.6 | 1679.4 | 1861.5 | 1510.7 | 1026.8 |
| Total Volume of Feeds (liters) | | 2.15 | 2.038 | 2.208 | 2.308 | 2.431 | 2.191 | 2.181 | 2.137 |
| Feed | $CCl_4:CH_2=CCl_2$ (mol:mol) | 1.999 | 1.110 | 2.002 | 3.257 | 1.822 | 2.030 | 2.043 | 1.122 |
| Ratios | $CuCl:CH_2=CCl_2$ (mol:mol) | 0.061 | 0.034 | 0.119 | 0.100 | 0.202 | 0.126 | 0.064 | 0.122 |
| | solvent:$CH_2=CCl_2$ (mol:mol) | 1.487 | 0.281 | 1.472 | 1.651 | 1.668 | 1.018 | 2.013 | 1.931 |
| Yields* | HCP (%) | 8.19% | 0.10% | 42.02% | 68.61% | 69.63% | 3.21% | 10.56% | 14.98% |
| | OCPc (%) | 0.06% | 0.00% | 2.71% | 5.16% | 8.55% | 0.19% | 0.13% | 0.09% |
| Space-time Yield HCPr (gmol/hr-liter) | | 0.12 | 0.00 | 0.65 | 0.79 | 1.07 | 0.05 | 0.15 | 0.26 |
| Product Ratios HCPr:OCPe (g:g) | | 203 | 42.5 | 22.4 | 19.2 | 11.7 | 24.0 | 120.3 | 233.0 |

| Example | | 9 | 10 | 11 | 12 | 13 | 14 | 15 |
|---|---|---|---|---|---|---|---|---|
| Elapsed Time (Hr) | | 1.6 | 1.6 | 1.6 | 16.8 | 1.6 | 4.8 | 1.6 |
| Avg. Temperature (°C.) | | 103 | 130 | 130 | 97 | 142 | 110 | 121 |
| Max. Temperature (°C.) | | 109 | 135 | 137 | 104 | 147 | 119 | 126 |
| Feeds | 1,1-dichloroethene (grams) | 764 | 615 | 466 | 576 | 480 | 548 | 600 |
| | butanenitrile (grams) | 553 | 835 | 672 | 832 | 668 | — | — |
| | copper (I) chloride (grams) | 48 | 36 | 59 | 72 | 116 | 34 | 73 |
| | acetonitrile (grams) | — | — | — | — | — | — | 372 |
| | propanenitrile (grams) | — | — | — | — | — | 477 | — |
| | tetrachloromethane (grams) | 1364 | 1042 | 1509 | 1021 | 1491 | 1745 | 1905 |
| Total Volume of Feeds (liters) | | 2.19 | 2.22 | 2.19 | 2.18 | 2.20 | 2.17 | 2.18 |
| Feed | $CCl_4:CH_2=CCl_2$ (mol:mol) | 1.125 | 1.068 | 2.042 | 1.117 | 1.957 | 2.006 | 2.002 |
| Ratios | $CuCl:CH_2=CCl_2$ (mol:mol) | 0.062 | 0.058 | 0.123 | 0.123 | 0.236 | 0.061 | 0.119 |
| | solvent:$CH_2=CCl_2$ (mol:mol) | 1.016 | 1.905 | 2.025 | 2.025 | 1.951 | 1.532 | 1.466 |
| Yields* | HCP (%) | 7.94% | 51.08% | 76.45% | 49.98% | 78.21% | 64.44% | 35.33% |
| | OCPc (%) | 0.02% | 12.43% | 7.16% | 4.75% | 7.17% | 10.25% | 3.25% |
| Space-time Yield HCPr (gmol/hr-liter) | | 0.18 | 0.91 | 1.05 | 0.08 | 1.10 | 0.64 | 0.63 |
| Product Ratios HCPr:OCPe (g:g) | | 585 | 6 | 15 | 15 | 16 | 9 | 16 |

*Yields are based on 1,1-dichloroethene fed

EXAMPLE 16:

A series of experiments were conducted to determine the thermal decomposition rate of HCPr in the purified stream.

124%/hour at 176.7° C. (350° F.). HCPr decomposition rates were also measured for these samples. HCPr decomposition rate was 0.1%/hour at 121.1° C. (250° F.), 1.5%/hour at 148.9° C. (300° F.), and 6.7%/hour at 162.8° C. (325° F.).

The higher decomposition rates of HCPr obtained in these experiments, in comparison to those obtained in the experiments described above, for the purified product are believed to be a result of the presence of iron contamination in the starting bottoms material. Although iron concentration was not measured, several hundred parts per million of iron was likely present. While the absolute rate of thermal decomposition of OCPe in an iron-free system is not available, it is clear from the experiments that OCPe is much more susceptible to thermal decomposition than HCPr.

While temperatures up to about 204.4° C. (400° F.) can be used in the inventive separation/purification process, temperatures exceeding 137.8° C. (280° F.) are preferably avoided, since thermal decomposition of HCPr and OCPe results in the loss of HCPr and in the formation of undesirable by-products. Removal of such by-products would require further steps to produce a purified HCPr product. Such additional purification steps would require additional equipment and would greatly increase the cost of the overall reaction.

EXAMPLE 18:

Distillation experiments were performed for the removal of lower boiling components from HCPr, higher boiling components and cuprous chloride. The analysis corresponded to flash unit or column 30, with the feed consisting of the effluent from reactor 20. A 32-tray Oldershaw column, corresponding to unit 30, was used in the experiments.

A reactor product consisting of 2665 g organic components and 58 g of CuCl catalyst was charged to the bottom reservoir of column 30. Batch distillation was conducted using a 1:1 ratio of reflux to overhead liquid draw. The final overhead pressure was 26 torr, and the final bottoms temperature was 111.1° C. (232° F.). The resulting separations of organic components is illustrated below in reference to Table 2.

TABLE 2

|  | Charge | Bottoms | Distillate |
|---|---|---|---|
| Total weight (grams) | 2665 | 998 | 1667 |
| Composition (wt %) | — | — | — |
| Vinylidene chloride | 2.2 | 0.0 | 3.6 |
| Carbon tetrachloride | 34.7 | 0.0 | 55.4 |
| Butanenitrile | 26.4 | 2.1 | 41.0 |
| 1,1,1,3,3-Pentachloropropene | 0.0 | 0.0 | 0.0 |
| Other light ends | 0.0 | 0.0 | 0.0 |
| 1,1,1,3,3-Hexachloropropane | 34.6 | 92.5 | 0.0 |
| 1,1,1,3,3,5,5,5-Octachloropentane | 2.0 | 5.2 | 0.0 |
| Other heavy ends | 0.1 | 0.2 | 0.0 |
| Total wt % | 100.0 | 100.0 | 100.0 |

The bottoms were observed to be free-flowing, and contained fine cuprous chloride solids which settled rapidly and were easily filtered. The solids recovered from filtering the distillation bottoms were found to dissolve readily into a solution of approximately 50% carbon tetrachloride and butanenitrile, corresponding to the distillate (stream 6 in FIG. 1). The resulting solution of recovered cuprous chloride in butanenitrile was used successfully as a feed to reactor 20 in a subsequent reaction process. Accordingly, the inventive method for purifying HCPr is particularly economical in view of the fact that the starting materials for the reaction can be recovered and reused.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for producing 1,1,1,3,3,3-hexachloropropane, comprising reacting tetrachloromethane and 1,1-dichloroethene in the presence of a copper chloride catalyst and a solvent selected from a C3 to a C5 alkanenitrile in a reactor, wherein the tetrachloromethane, 1,1-dichloroethene, catalyst and solvent are present in relative amounts sufficient to produce 1,1,1,3,3,3-hexachloropropane.

2. The method according to claim 1, wherein the copper chloride catalyst is cuprous chloride, cupric chloride, or a mixture thereof.

3. The method according to claim 1, wherein the solvent selected from a C3 to a C5 alkanenitrile is substituted with an alkyl or alkoxy group or a fluorine atom.

4. The method according to claim 1, wherein the solvent selected from a C3 to a C5 alkanenitrile has a boiling point less than 206° C.

5. The method according to claim 1, wherein the solvent is propanenitrile, butanenitrile, pentanenitrile, 2-methylpropanenitrile or 3-methoxypropanenitrile.

6. The method according to claim 5, wherein the solvent is butanenitrile.

7. The method according to claim 1, wherein the reaction takes place at a temperature in the range of from about 80° to 150° C.

8. The method according to claim 7, wherein the reaction takes place at a temperature in the range of from about 110° to 150° C.

9. The method according to claim 1, wherein the tetrachloromethane and 1,1-dichloroethene are introduced in a molar ratio in the range of from about 1.0:1 to 3.3:1, tetrachloromethane:1,1-dichloroethene.

10. The method according to claim 9, wherein the tetrachloromethane and 1,1-dichloroethene are introduced in a molar ratio in the range of from about 1.1:1 to 2.0:1, tetrachloromethane:1,1-dichloroethene.

11. The method according to claim 1, wherein the catalyst and 1,1-dichloroethene are introduced in a molar ratio in the range of from about 0.01:1 to 0.5:1, catalyst:1,1-dichloroethene.

12. The method according to claim 11, wherein the catalyst and 1,1-dichloroethene are introduced in a molar ratio in the range of from about 0.06:1 to 0.24:1, catalyst:1,1-dichloroethene.

13. The method according to claim 1, wherein the solvent and 1,1-dichloroethene are introduced in a molar ratio in the range of from about 0.05:1 to 10:1, solvent:1,1-dichloroethene.

14. The method according to claim 13, wherein the solvent and 1,1-dichloroethene are introduced in a molar ratio in the range of from about 0.5:1 to 3.0:1, solvent:1,1-dichloroethene.

15. The method according to claim 14, wherein the solvent and 1,1-dichloroethene are introduced in a molar ratio in the range of from about 1.4:1 to 2.0:1, solvent:1,1-dichloroethene.

16. The method according to claim 1, wherein the reaction is performed in a batch mode.

17. The method according to claim 1, wherein the reaction is performed in a semibatch mode.

18. The method according to claim 17, wherein the 1,1-dichloroethene is fed continuously to the reaction mixture.

19. The method according to claim 17, wherein the 1,1-dichloroethene is intermittently fed to the reaction mixture.

20. The method according to claim 1, wherein the reaction is performed continuously.

21. The method according to claim 1, wherein a reaction effluent is isolated, said reaction effluent comprising the 1,1,1,3,3,3-hexachloropropane, any unreacted tetrachloromethane and/or 1,1-dichloroethene, the catalyst, and the solvent, the method further comprising substantially separating the 1,1,1,3,3,3-hexachloropropane from the tetrachloromethane, the 1,1-dichloroethene, the catalyst, and the solvent.

22. The method according to claim 21, further comprising recovering and recycling to the reactor at least a portion of one or more of the tetrachloromethane, the 1,1-dichloroethene, the catalyst, and the solvent.

23. The method according to claim 1, wherein a reaction effluent is separated into two portions, the first portion comprising any unreacted tetrachloromethane and/or 1,1-dichloroethene, and the solvent, and the second portion comprising the catalyst, the 1,1,1,3,3,3-hexachloropropane, and a 1,1,1,3,3,5,5,5-octachloropentane byproduct, if present.

24. The method according to claim 23, wherein the reaction effluent separation is performed in a vacuum flash vessel or column, and the first portion is flashed overhead and the second portion is a vessel or column bottoms.

25. The method according to claim 23, further comprising separating catalyst particles in the second portion from a liquid comprising the 1,1,1,3,3,3-hexachloropropane and 1,1,1,3,3,5,5,5-octachloropentane.

26. The method according to claim 25, further comprising recycling the separated catalyst particles to the reactor.

27. The method according to claim 26, further comprising redissolving the separated catalyst particles in at least a part of the first portion, thereby forming a first recycle stream, and recycling the first recycle stream comprising the separated catalyst particles to the reactor.

28. The method according to claim 26, wherein the first portion is introduced into a distillation column, and the unreacted tetrachloromethane and/or 1,1-dichloroethene is separated overhead from the solvent, and the solvent is a column bottoms, and further comprising redissolving the separated catalyst particles in at least a part of the column bottoms, thereby forming a first recycle stream, and recycling the first recycle stream comprising the separated catalyst particles to the reactor.

29. The method according to claim 25, further comprising redissolving the separated catalyst particles in at least a part of the first portion, thereby forming a first recycle stream, and recycling the first recycle stream comprising the separated catalyst particles to the reactor.

30. The method according to claim 25, further comprising separating the liquid comprising the 1,1,1,3,3,3-hexachloropropane and 1,1,1,3,3,5,5,5-octachloropentane by distillation into an overhead product comprising the 1,1,1,3,3,3-hexachloropropane and a bottoms comprising the 1,1,1,3,3,5,5,5-octachloropentane.

31. The method according to claim 30, wherein the 1,1,1,3,3,3-hexachloropropane is further purified by distillation.

32. The method according to claim 21, wherein the 1,1,1,3,3,3-hexachloropropane separation is performed at a temperature of about 204.4° C. or less.

33. The method according to claim 32, wherein the 1,1,1,3,3,3-hexachloropropane separation is performed at a temperature of about 137.8° C. or less.

* * * * *